United States Patent [19]

Sturm et al.

[11] Patent Number: 5,080,899

[45] Date of Patent: Jan. 14, 1992

[54] METHOD OF TREATING PULMONARY INFLAMMATION

[75] Inventors: Robert J. Sturm, Lawrenceville, N.J.; Laurel M. Adams, Durham, N.C.; Barry M. Weichman, Skillman, N.J.

[73] Assignee: American Home Products Corporation, New York, N.Y.

[21] Appl. No.: 659,782

[22] Filed: Feb. 22, 1991

[51] Int. Cl.$^5$ .................. A61K 35/74; A61K 31/44
[52] U.S. Cl. .................................. 424/122; 514/291
[58] Field of Search .................. 424/122; 514/291

[56] References Cited

U.S. PATENT DOCUMENTS 3,929,992 12/1975 Sehgal et al. .................. 424/122

OTHER PUBLICATIONS

Abstract of Areugi (Jap. J. Allergology) 39(5):483 (1990).
Am. Rev. Resp. Dis. 131:373 (1985).
J. Allergy Clin. Immunol. 85:533 (1990).
Am. Rev. Resp. Dis. 140:225 (1989).
J. Immunol. 141:4158 (1988).
Can. J. Physiol. Pharmacol. 55, 48 (1977).
FASEB 3,3411 (1989).
Med. Sci. Res. 17:877 (1989).
Chemical Abstracts 87:111825p (1977).

*Primary Examiner*—Jerome D. Goldberg
*Attorney, Agent, or Firm*—Richard K. Jackson

[57] ABSTRACT

This invention provides a method of preventing or reversing pulmonary inflammation in a mammal by administering an effective amount of rapamycin orally, parenterally, intranasally, or intrabronchially. As such, rapamycin is useful in providing the symptomatic relief of diseases in which pulmonary inflammation is a component such as, asthma, chronic obstructive pulmonary disease, emphysema, acute respiratory distress syndrome, bronchitis, and the like.

8 Claims, No Drawings

METHOD OF TREATING PULMONARY INFLAMMATION

BACKGROUND OF THE INVENTION

Asthma has recently been recognized as being mediated by an inflammatory response in the respiratory tract [DeMonchy, J., Am. Rev. Resp. Dis. 131: 373-376 (1985)]. Recent findings suggest that human T-lymphocytes play a major role in regulating the airway inflammation associated with allergic asthma [Frew, A. J., J. Allergy Clin. Immunol. 85: 533-539 (1990)] and chronic obstructive pulmonary disease [O'Connor, G. T., Am. Rev. Resp. Dis. 140: 225-252 (1989)].

In addition to the infiltration of other inflammatory cells into the pulmonary system, human asthmatics and atopics who are dual responders (i.e., show both early and late phase reactions) show a small but significant infiltration of T-lymphocytes following antigen challenge [Frew, A. J., and Kay, A. B., J. Immunol. 141: 4158-4164 (1988)]. More importantly, these recruited T-lymphocytes are almost entirely of the CD4+ (T-helper) type, and there appears to be a direct correlation between the influx of CD4+ cells, the influx of eosinophils, and the IgE-related allergic response in these individuals [Frew, A. M. and Kay, A. B., J. Immunol. 141: 4158-4164 (b 1988)]. In severe asthmatics, these CD4+ cells appear to be activated [Corrigan, C. J. and Kay, A. B. Am. Rev. Resp. Dis. 141: 970-977 (1990)] by virtue of the increase in IL-2 receptor positive cells. Thus, these cells are capable of producing cytokines (such as IL-3, IL-5, and granulocyte macrophage colony stimulating factor) which can directly affect the differentiation, maturation and activation state of the eosinophils and other inflammatory cells.

Rapamycin, a macrocyclic triene antibiotic produced by *Streptomyces hygroscopicus* [U.S. Pat. No. 3,929,992] has been shown to prevent the formation of humoral (IgE-like) antibodies in response to an albumin allergic challenge [Martel, R., Can. J. Physiol. Pharm. 55: 48 (1977)], inhibit murine T-cell activation [Strauch, M., FASEB 3: 3411 (1989)], and prolong survival time of organ grafts in histoincompatable rodents [Morris, R., Med. Sci. Res. 17:877 (1989)].

DESCRIPTION OF THE INVENTION

This invention provides a method of preventing or reversing pulmonary inflammation in a mammal by administering an effective amount of rapamycin orally, parentally, nasally, or intrabronchially. As such, rapamycin is useful in providing the symptomatic relief of diseases in which pulmonary inflammation is a component such as, asthma, chronic obstructive pulmonary disease, emphysema, acute respiratory distress syndrome, bronchitis, and the like.

The prevention and reversal of pulmonary inflammation by rapamycin was established by the inhibition of pulmonary inflammatory cell influx in an in vivo standard pharmacological test procedure emulating the inflammatory changes observed clinically in chronic asthmatics. The procedure used and results obtained are described below.

Male Hartley guinea pigs (400-700 g) that have been fasted overnight are sensitized according to a modification of the method of Dunn et al [Am. Rev. Resp. Dis 137: 541 (1988)]. Guinea pigs receive 1 i.m. injection in each hind leg of 0.35 ml (total volume =0.7 ml) ovalbumin (OA; 50 mg/ml), in isotonic sterile saline. Following a 3 week sensitization period, each animal is pretreated ($-1$ h) with pyrilamine (2.5 mg/kg i.p.) to prevent hypoxic collapse and death, and then challenged with an aerosol of 0.2% OA (in distilled deionized water) for 3 min using a DeVilbiss Ultra-Neb 100 nebulizer. Drugs or vehicle (0.5% Tween 80) are administered orally in a volume of 1 ml/500 g body wt. at appropriate times pre- and post- OA challenge. Rapamycin was administered orally at $-48$ h, $-24$ h, $-1$ h and $+4$ hours relative to OA aerosol. Positive control animals were challenged with the OA aerosol, and negative control animals were challenged with an aerosol of distilled water only.

Twenty-four hours later, each animal was humanely sacrificed with an overdose of urethane (60 mg/ml, ~10 ml i.p.). The trachea of each animal is isolated and the lungs are lavaged in situ with three-20 ml washes if isotonic sterile saline. All samples are kept on ice. This bronchoalveolar lavage fluid from each animal is then centrifuged for 10 min at 400 $\times$g at 5° C. The supernatant is discarded, and each cell pellet is resuspended in 3 ml of isotonic sterile saline. The number of inflammatory cells present was then determined using a Coulter model ZM particle counter.

All values are corrected by subtracting the mean ($\bar{x}$) value of the negative control group from all other individual samples. Percent inhibition values for individual samples are calculated using these corrected cell counts in the following formula:

$$\% \text{ Inhibition} = \frac{\bar{x} \text{ positive control (corrected)} - \text{individual cell count (corrected)}}{\bar{x} \text{ positive control (corrected)}} \times 100$$

Mean % inhibition is determined for each group and expressed as $\bar{x}$% inhibition $\pm$S. E. The ED$_{50}$s with 95% confidence limits are calculated [Litchfield, S. T. and Wilcoxon, F. A., J. Pharmacol. Exp. Ther. 96: 99-113 (1949)].

The following table shows the results obtained for guinea pigs treated with various doses of rapamycin (n=12 animals per treatment group).

INHIBITION OF PULMONARY INFLAMMATORY CELL INFLUX

| Rapamycin Dose (mg/kg, p.o.) | Percent Inhibition (mean + std. error) |
| --- | --- |
| 4.0 | 88.1 $\pm$ 5.8 |
| 1.0 | 71.5 $\pm$ 13.6 |
| 0.3 | 64.3 $\pm$ 8.2 |
| 0.1 | 43.9 $\pm$ 15.0 |
| 0.03 | 13.5 $\pm$ 20.6 |

The results of this in vivo standard pharmacological test procedure emulating the inflammatory cell changes observed clinically in asthmatics, demonstrates that rapamycin exhibited a dose dependent inhibition of pulmonary inflammatory cell influx with a calculated ED$_{50}$(95% C. L.) of 0.2 (0.08-0.60) mg/kg in response to an antigenic challenge, and is therefore useful in preventing or reversing pulmonary inflammation and in treating disease states in which pulmonary inflammation is a component such as, asthma, chronic obstructive pulmonary disease, emphysema, acute respiratory distress syndrome, bronchitis, and the like.

When rapamycin is employed in the treatment of pulmonary inflammation, it can be formulated into oral dosage forms such as tablets, capsules and the like. Rapamycin can be administered alone or by combining it with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. Rapamycin may be encapsulated with or without other carriers. In all cases, the proportion of active ingredients in said compositions both solid and liquid will be at least to impart the desired activity thereto on oral administration. Rapamycin may also be injected parentally, in which case it is used in the form of a sterile solution containing other solutes, for example, enough saline or glucose to make the solution isotonic. For administration by intranasal or intrabronchial inhalation or insufflation, rapamycin may be formulated into an aqueous or partially aqueous solution, which can then be utilized in the form of an aerosol.

The dosage requirements vary with the particular compositions employed, the route of administration, the severity of the symptoms presented and the particular subject being treated. Based on the results obtained in the standard pharmacological test procedure, projected oral daily dosages of active compound would be 0.01 $\propto$ 10 mg/kg, preferably between 0.1-10 mg/kg, and more preferably between 0.3-4 mg/kg. Treatment will generally be initiated with small dosages less than the optimum dose of the compound. Thereafter the dosage is increased until the optimum effect under the circumstances is reached; precise dosage for oral, parenteral, nasal, or intrabronchial administration will be determined by the administering physician based on experience with the individual subject treated. In general, rapamycin is most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of preventing or reversing pulmonary inflammation in a mammal in need thereof which comprises administering to said mammal an effective amount of rapamycin orally, parentally, intranasally, or intrabronchially.

2. The method according to claim 1, which comprises administering rapamycin in a daily dose of 0.01 to 10 mg/kg.

3. The method according to claim 1, which comprises administering rapamycin in a daily dose of 0.1 to 10 mg/kg.

4. The method according to claim 1, which comprises administering rapamycin in a daily dose of 0.3 to 4 mg/kg.

5. A method of providing symptomatic relief of asthma, chronic obstructive pulmonary disease, emphysema, acute respiratory distress syndrome, and acute bronchitis in a mammal in need thereof which comprises administering to said mammal an effective amount of rapamycin orally, parentally, intranasally, or intrabronchially.

6. The method according to claim 5, which comprises administering rapamycin in a daily dose of 0.01 to 10 mg/kg.

7. The method according to claim 5, which comprises administering rapamycin in a daily dose of 0.1 to 10 mg/kg.

8. The method according to claim 5, which comprises administering rapamycin in a daily dose of 0.3 to 4 mg/kg.

* * * * *